US00PP12066P2

(12) United States Plant Patent
Oliver

(10) Patent No.: US PP12,066 P2
(45) Date of Patent: Aug. 28, 2001

(54) HEUCHERA PLANT NAMED 'SILVER SCROLLS'

(76) Inventor: Charles G. Oliver, 921 Scottdale-Dawson Rd., Scottdale, PA (US) 15683

( * ) Notice: Subject to any disclaimer, the term of this patent is extended or adjusted under 35 U.S.C. 154(b) by 0 days.

(21) Appl. No.: 09/460,005

(22) Filed: Dec. 13, 1999

(51) Int. Cl.[7] ..... A01H 5/00
(52) U.S. Cl. ..... Plt./263

(58) Field of Search ..... Plt./263

*Primary Examiner*—Bruce R. Campell
*Assistant Examiner*—Annette H. Para
(74) *Attorney, Agent, or Firm*—C. A. Whealy

(57) ABSTRACT

A distinct cultivar of Heuchera plant named 'Silver Scrolls', characterized by its proporational plants with respect to quantity of flowers to foliage density; unique leaf coloration: silvery-metallic with tracings of dark veins; numerous showy white flowers on erect cylindrical-shaped panicles; and excellent garden performance.

2 Drawing Sheets

BACKGROUND OF THE INVENTION

The present invention relates to a new and distinct cultivar of Heuchera, botanically known as Heuchera sp., and hereinafter referred to by the cultivar name Silver Scrolls.

The new cultivar is a product of a planned breeding program conducted by the Inventor in Scottdale, Pa. The objective of the breeding program is to create new Heuchera cultivars having good vigor and uniform plant habit; showy and attractive flowers; attractive silvery-metallic foliage; and good garden performance.

The new cultivar was selected by the Inventor in Scottdale, Pa., from seedling progeny from the Inventor's cross made in 1996 of the Heuchera sp. cultivar Harmonic Convergence, disclosed in U.S. Plant Pat. No. 11,111, as the male or pollen parent with the Heuchera sp. cultivar Petite Bronze Pearl (unpatented) as the female or seed parent.

Asexual reproduction of the new cultivar by divisions and by cuttings taken at Scottdale, Pa., has shown that the unique features of this new Heuchera plant are stable and reproduced true to type in successive generations of asexual reproduction.

SUMMARY OF THE INVENTION

The new Heuchera plant has not been observed under all possible environmental conditions. The phenotype may vary significantly with variations in environment such as temperature, light level, nutritional and water status without, however, any variance in genotype.

The following traits have been repeatedly observed and are determined to be the unique characteristics of 'Silver-Scrolls'. These characteristics in combination distinguish the new Heuchera plant as a new and distinct cultivar:

1. Proportional plants with respect to quantity of flowers to foliage density.

2. Unique leaf coloration: silvery-metallic with tracings of dark veins.

3. Numerous showy white flowers on erect cylindrical-shaped panicles.

4. Excellent garden performance.

In side-by-side comparisons in Scottdale, Pa., under commercial practice, plants of the new Heuchera differ from plants of the male parent, the cultivar Harmonic Convergence, in the following characteristics:

1. Plants of the new Heuchera have cylindrical-shaped panicles that are held upright whereas plants of the new cultivar Harmonic Convergence have conical-shaped panicles that are held perpendicular to about 45° from vertical.

2. Foliage of plants of the new Heuchera has a silvery metallic sheen whereas foliage of plants of the cultivar Harmonic Convergence does not have a metallic sheen.

3. Flowers of plants of the new Heuchera are white in color whereas plants of the Harmonic Convergence have pink-colored flowers.

4. Plants of the cultivar Harmonic Convergence have exerted styles and recurved petals whereas plants of the new Heuchera do not have exerted styles no recurved petals.

In side-by-side comparisons in Scottdale, Pa., under commercial practice, plants of the new Heuchera are different from plants of the female parent, the cultivar Petite Bronze Pearl in the following characteristics:

1. Plants of the new Heuchera are larger with larger inflorescences and larger leaves than plants of the cultivar Petite Bronze Pearl.

2. Foliage of plants of the new Heuchera is mostly silvery metallic with dark veins whereas foliage of plants of the cultivar Petite Bronze Pearl are uniformly bronze-green in color.

3. Flowers of plants of the new Heuchera are white in color whereas plants of Petite Bronze Pearl have light pink-colored flowers.

4. Plants of the cultivar Petite Bronze Pearl have exerted styles whereas plants of the new Heuchera do not have exerted styles.

Plants of the new Heuchera can be compared to plants of the commercial cultivar Pewter Veil, disclosed in U.S. Plant Pat. No. 8,984. In side-by-side comparisons in Scottdale, Pa., under commercial practice, plants of the new Heuchera are different from plants of the cultivar Pewter Veil in the following characteristics:

1. Plants of the new Heuchera have cylindrical-shaped panicles that are held upright whereas panicles of plants of the cultivar Pewter Veil have an open habit and are outwardly spreading.

2. Foliage of plants of the new Heuchera is mostly silvery metallic with dark veins whereas foliage of plants of the cultivar Pewter Veil has small areas of metallic coloration suffused with purple.

3. Flowers of plants of the new Heuchera are white in color whereas plants of the Pewter Veil have yellowish green-colored flowers.

4. Flowering stems of plants of the new Heuchera are more suitable for cut flowers than flowering stems of plants of the cultivar Pewter Veil.

Plants of the new Heuchera can be compared to plants of the nonpatented commercial cultivar Palace Purple. In side-by-side comparisons in Scottdale, Pa., under commercial practice, plants of the new Heuchera differ from plants of the cultivar Palace Purple in the following characteristics:

1. Plants of the new Heuchera have panicles that are held upright whereas panicles of plants of the cultivar Palace Purple are freely spreading.

2. Foliage of plants of the new Heuchera is mostly silvery metallic with dark veins whereas foliage of plants of the cultivar Palace Purple are uniformly bronze-purple in color.

3. Foliage color of plants of the new Heuchera is retained under high light and temperatures conditions whereas foliage color of plants of the cultivar Palace Purple fades to bronze-green under high light and temperatures conditions.

4. Flowers of plants of the new Heuchera are white in color whereas plants of Palace Purple have green-colored flowers.

5. Flowering stems of plants of the new Heuchera are more suitable for cut flowers than flowering stems of plants of the cultivar Palace Purple.

BRIEF DESCRIPTION OF THE PHOTOGRAPHS

The accompanying colored photographs illustrates the overall appearance of the new cultivar, showing the colors as true as it is reasonably possible to obtain in colored reproductions of this type. Colors in the photographs may differ slightly from the color values cited in the detailed botanical description which more accurately describe the actual colors of the new Heuchera.

The photograph on the first sheet comprises a top perspective view of a typical plant of 'Silver Scrolls'.

The photograph at the top of the second sheet comprises a close-up view of typical leaves of 'Silver Scrolls'.

The photograph at the bottom of the second sheet comprises a close-up view of a typical flower stem of 'Silver Scrolls'.

DETAILED BOTANICAL DESCRIPTION

The following observations, measurements, values, and comparisons describe plants grown in Scottdale, Pa., in a glass-covered greenhouse with day temperatures ranging from 16 to 27° and night temperatures ranging from 4 to 16° C. depending upon the season. Plant used for the description and the photography was about nine month old. In the following description, color references are made to The Royal Horticultural Society Colour Chart except where general terms of ordinary dictionary significance are used.

Classification: Botanical: Heuchera sp. cultivar Silver Scrolls.

Parentage:

*Male or pollen parent.*—Heuchera sp cv. Harmonic Convergence, disclosed in U.S. Plant Pat. No. 11,111.

*Female or seed parent.*—Heuchera sp. cv. Petite Bronze Pearl (unpatented).

Propagation:

*Type.*—By divisions, by cuttings or by tissue culture.

*Time to initiate roots.*—About 14 days at temperatures of 21° C.

*Time to develop roots.*—About 30 days at temperatures of 21° C.

*Root description.*—Young plants, fibrous; older plants becoming woody.

Plant description:

*Plant form and growth habit.*—Perennial, rounded foliage with numerous upright and strong flowering stems.

*Vigor.*—Vigorous, rapid growth rate.

*Crop time.*—From cuttings or rooted tissue-cultured plantlets, about nine months are required to produce mature flowering plants. Plants typically produced in 15-cm containers.

*Plant height, soil level to top of foliage.*—About 13.5 cm.

*Plant height, soil level to top of flowers.*—About 67.5 cm.

*Plant diameter.*—About 42.5 cm.

Foliage description:

*Arrangement.*—Rosette, single.

*Length.*—About 7 cm.

*Width.*—About 6 cm.

*Shape.*—Rounded cordate, 7-lobed.

*Apex.*—Broadly obtuse, lobed.

*Base.*—Cordate.

*Margin type.*—Crenate, ciliate.

*Venation pattern.*—Reticulate.

*Texture.*—Slightly rough, slight pubescence on lower surface.

*Color.*—Marbled effect of silvery-metallic with tracings of dark veins. Young foliage, upper surface: 198A, underlain with 187B. Young foliage, lower surface: 187B. Mature foliage, upper surface: 198A. Mature foliage, lower surface: 187B. Venation, upper surface: 189A underlain with 200A. Venation, lower surface: 187B.

*Petiole.*—Length: About 12 cm. Diameter: About 2 mm. Color: 187B.

*Durability of foliage to stress.*—High.

Flower description:

*Natural flowering season.*—Late spring and early summer, May and June in the Northern Hemisphere.

*Flower arrangement.*—Numerous single flowers arranged on erect feathery cylindrical panicles on upper half of flowering stem; usually about 100 to 150 flowers per flowering stem. Flowering stems uniform in shape and dense with numerous flowers. Flowering continuous with numerous flowering stems forming throughout the flowering period; usually about 3 to 10 flowering stems per plant.

*Flowering stem length.*—About 30 to 35 cm.

*Flower appearance.*—Campanulate, persistent. Individual flowers last about one week on plant.

*Fragrance.*—None detected.

*Flower diameter.*—About 5 mm.

*Flower depth (height).*—About 6.5 mm.

*Flower bud.*—Length: About 4 mm. Diameter: About 2.5 mm. Shape: Bulbous. Color: 57D. Rate of opening: About 2 to 3 days.

*Petals.*—Appearance: Thin. Texture: Slightly pubescent. Arrangement: Radially symmetrical with five petals. Shape: Spatulate. Apex: Acute. Margin: Entire. Length: About 3 mm. Width: About 1 mm. Color: When opening and fully opened, inner surface: White, close to 155D. When opening and fully opened, outer surface: White, close to 155D.

*Sepals/calyx.*—Appearance: Five sepals fused into a radially symmetrical calyx tube. Sepal apex: Obtuse. Sepal margin: Entire. Sepal texture: Thin, pubescent. Sepal color: Upper surface: White, close to 155D. Lower surface: Distal, white, close to 155D; proximal, 57D; scattered hairs, tipped with 57D. Calyx length: About 6 mm. Calyx diameter: About 5 mm.

*Peduncles.*—Length (crown of plant to lowest flowers): About 32.5 cm. Angle: Erect, upright. Strength: Strong. Color: 187B.

*Reproductive organs.*—Androecium: Stamen number: Five. Anther shape: Oval. Anther size: About 0.2 mm. Anther color: 25A. Amount of pollen: Scarce. Pollen color: 23B. Gynoecium: Pistil number: Two. Pistil length: About 5 mm. Stigma shape: Rounded. Stigma color: 157C. Style length: About 3 mm. Style color: 157D. Ovary color: 157D.

*Seed description.*—Length: About 0.6 mm. Diameter: About 0.3 mm. Color: Black, close to 202A.

Disease resistance: Under commercial conditions, resistance to diseases common to Heuchera has not been observed.

It is claimed:

1. A new and distinct Heuchera plant named 'Silver Scrolls', as illustrated and described.

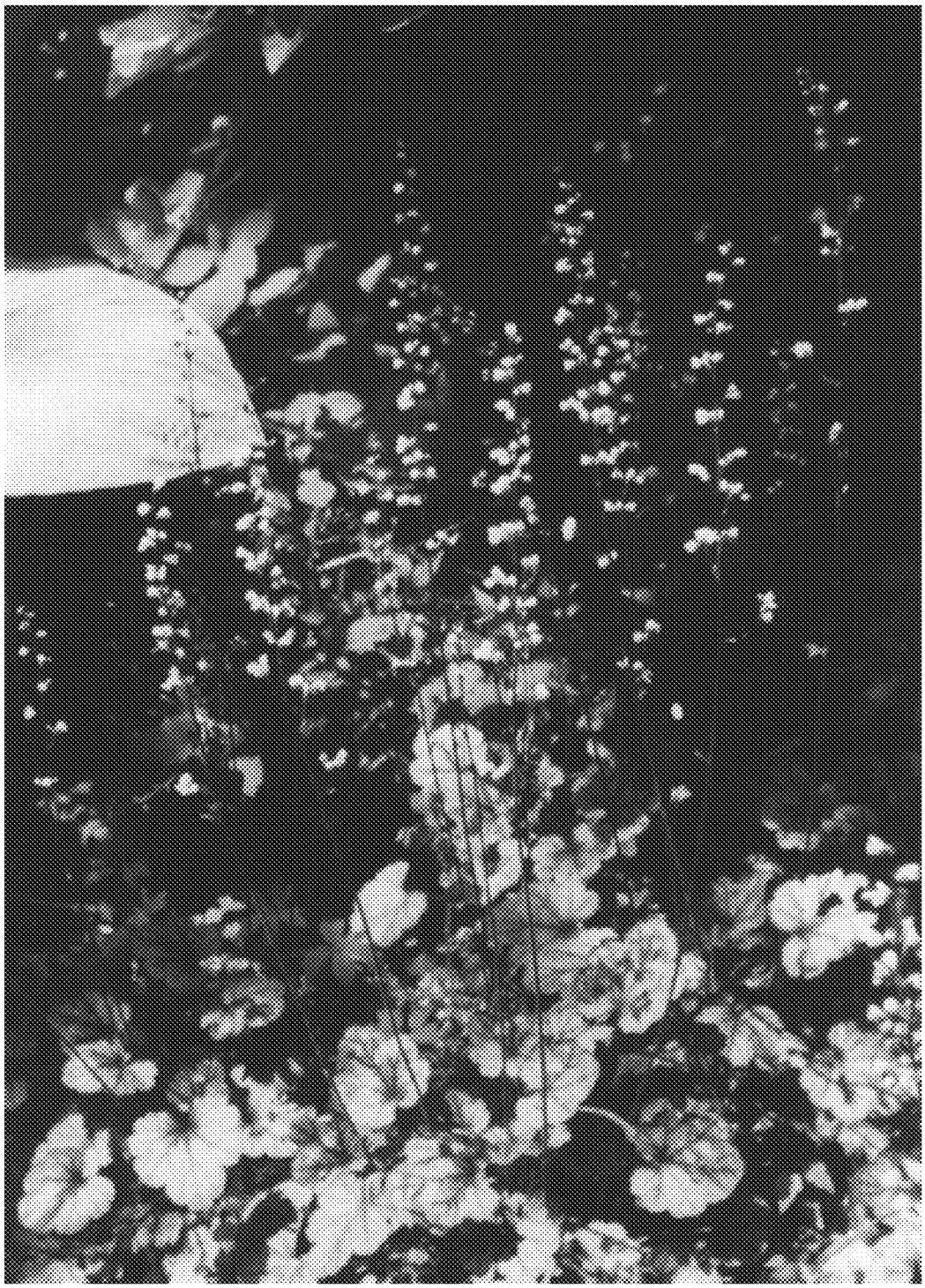

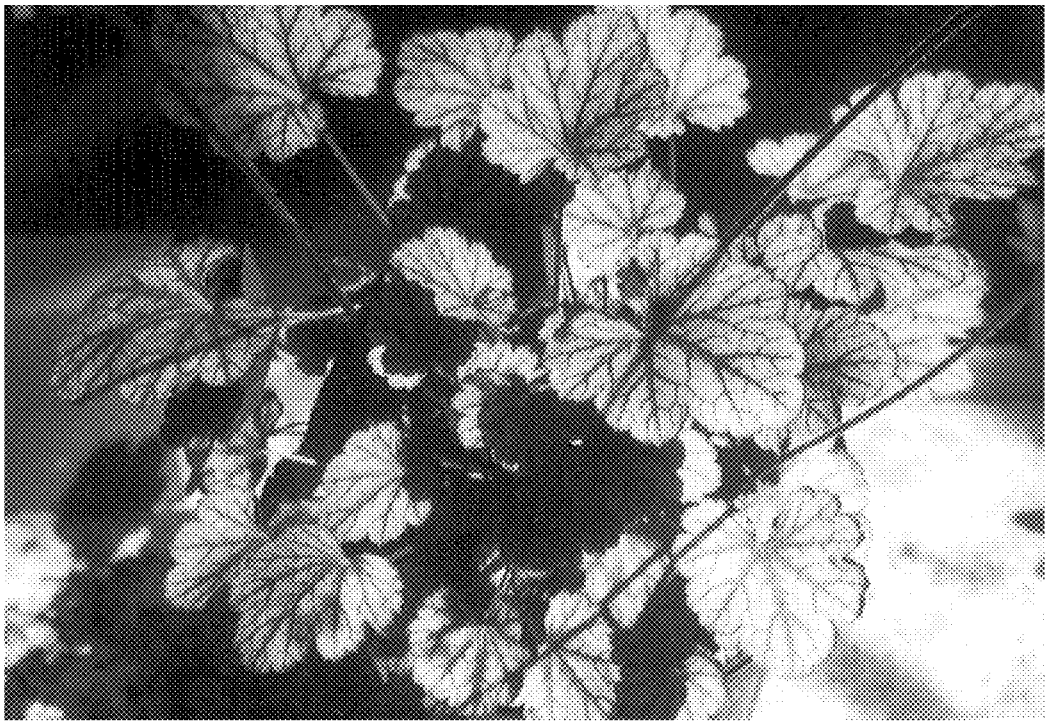
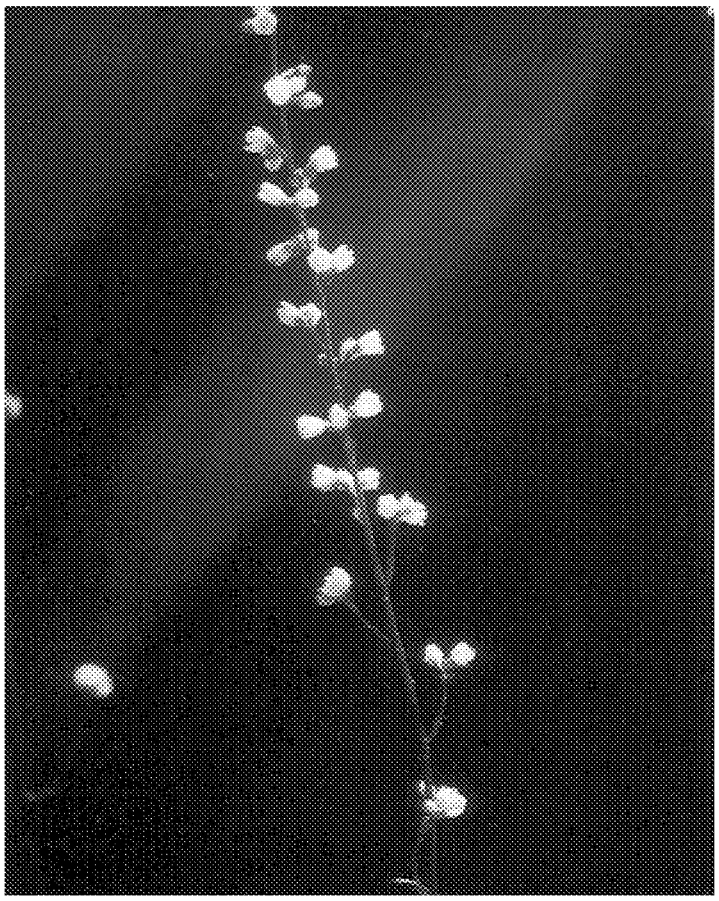

* * * * *